United States Patent
Kink et al.

(10) Patent No.: US 7,894,900 B2
(45) Date of Patent: Feb. 22, 2011

(54) DEVICE AND METHOD FOR MONITORING CARDIAC PACING RATE

(75) Inventors: Andres Kink, Kiili (EE); Mart Min, Tallinn (EE); Toomas Parve, Tallinn (EE); Indrek Rätsep, Keila (EE)

(73) Assignee: Smartimplant OÜ, Tallinn (EE)

(*) Notice: Subject to any disclaimer, the term of this patent is extended or adjusted under 35 U.S.C. 154(b) by 719 days.

(21) Appl. No.: 11/847,430

(22) Filed: Aug. 30, 2007

(65) Prior Publication Data

US 2008/0058882 A1    Mar. 6, 2008

Related U.S. Application Data (60) Provisional application No. 60/823,965, filed on Aug. 30, 2006.

(51) Int. Cl.
A61B 5/08 (2006.01)
A61N 1/08 (2006.01)
A61N 1/365 (2006.01)

(52) U.S. Cl. ............. 607/17; 607/24; 600/481; 600/482; 600/483; 600/484; 600/485

(58) Field of Classification Search ......... 600/481–485; 607/24

See application file for complete search history.

(56) References Cited

U.S. PATENT DOCUMENTS

| | | | | |
|---|---|---|---|---|
| 5,046,502 | A * | 9/1991 | Kunig | 600/483 |
| 6,885,892 | B1 * | 4/2005 | Min et al. | 607/24 |
| 6,975,903 | B1 | 12/2005 | Min et al. | |
| 7,614,998 | B2 * | 11/2009 | Gross et al. | 600/17 |
| 2006/0100539 | A1 | 5/2006 | Min et al. | |
| 2006/0149152 | A1 * | 7/2006 | Amitzur et al. | 600/485 |
| 2006/0184060 | A1 * | 8/2006 | Belalcazar et al. | 600/547 |

OTHER PUBLICATIONS

Webster, J.G., "Design of Cardiac Pacemakers", IEEE Press, 1995, Piscataway, NJ.
Ericsson, A.B., "Cardioplegia and Cardiac Function Evaluated by Left Ventricular Pressure-Volume Relations", 2000, pp. 1-76, Karolinska Institutet, Stockholm, Sweden.
Soderqvist, E., "Left Ventricular Conductance Volumetry Technique Applied to a Pressure Guide Wire", Licentiate Thesis, 2002, pp. 1-47, Royal Institute of Technology, Stockholm, Sweden.

(Continued)

*Primary Examiner*—Carl H Layno
*Assistant Examiner*—Natasha N Patel
(74) *Attorney, Agent, or Firm*—Vern Maine & Associates (57) ABSTRACT

A device for monitoring cardiac pacing rate having a measuring unit for receiving an electrical signal representing the patient's cardiac demand, and a computing unit for determining the myocardial energy balance by calculating energy consumed by the myocardium for both an external dynamic work for pumping blood into a vascular system, and an internal static work of the myocardium. Volume and time based measurements are used, and in one embodiment, volumes are estimated and volume ratios are calculated from volume estimates. In another embodiment, volumes are estimated from bioimpedance measurements. A further aspect is a rate adaptive pacemaker, wherein the maximum pacing rate is determined from the myocardial energy balance such that the energy supplied to the myocardium approximately equals the energy consumed by the myocardium for both an external dynamic work for pumping blood into a vascular system and an internal static work of the myocardium.

23 Claims, 6 Drawing Sheets

OTHER PUBLICATIONS

Denslow, S., "Relationship Between PVA and Myocardial Oxygen Consumption Can Be Derived From Thermodynamics", The American Physiological Society, 1996, pp. H730-H740, vol. 270, Issue 2.

Salo, R., "Application of Impedance Volume Measurement to Implantable Devices", International Journal of Bioelectromagnetism, 2003, pp. 1-5, vol. 5, No. 1.

Salo, R., "Accuracy of Conductance Catheter Measurements in a Realistic Numerical Heart Model: Validation of Reciprocal Equivalent Distance Extrapolation", International Journal of Bioelectromagnetism, 2003, pp. 1-3, vol. 5, No. 1.

Salo, R. et al., "The Use of Intracardiac Impedance-Based Indicators to Optimize Pacing Rate", In Critical Cardiac-Pacing, 1995, pp. 234-249, W.B. Saunders Co., Philadelphia, PA.

Salo, R., "The Theoretical Basis of a Computational Model for the Determination of Volume by Impedance", Automedica, 1989, pp. 299-309, vol. 11.

* cited by examiner

DEVICE AND METHOD FOR MONITORING CARDIAC PACING RATE

CROSS REFERENCE TO RELATED APPLICATIONS

This application claims the benefit of U.S. provisional application 60/823,965, filed on Aug. 30, 2006, the subject matter of which is herein incorporated by reference for all purposes.

TECHNICAL FIELD

The invention relates to the field of cardiovascular methods and devices for determining the pace rate from patient's myocardial energy balance, i.e. from the demand of the patient's organism and external and internal work of the myocardium. The invention can be used in various embodiments such as in rate-adaptive pacemakers. The energy balance can be determined from volume or volume ratio and time measurements, while electrical bioimpedance can be used to measure or to estimate the volume or volume ratio.

BACKGROUND OF THE INVENTION

There are multiple approaches for controlling a pacing rate of a rate-adaptive pacemaker to provide a heart rate adequate to meet the metabolic demand (J. G. Webster, Design of Cardiac Pacemaker. Piscataway, N.J.: IEEE Press, 1995.). Different sensors have been used to assess metabolic demands (workload of the body $W_{Body}$), including body acceleration and movement activity and transthoracic bioimpedance to estimate minute volume MV (see also FIG. 1). Minute ventilation, the product of breathing rate and tidal volume, correlates well with workload $W_{body}$. An ideal rate-adaptive pacing system would automatically control upper and lower rate limits to prevent over pacing (M. Min, A. Kink, T. Parve, "Rate adaptive pacemaker," U.S. Pat. No. 6,885,892, Apr. 26, 2005.) and under pacing (M. Min, A. Kink, T. Parve, "Rate adaptive pacemaker using impedance measurements and stroke volume calculations," U.S. Pat. No. 6,975,903, Dec. 13, 2005). These patents are incorporated herein by reference for all purposes.

Over pacing can take two forms. In the first form, the paced heart rate is too high for normal ventricular filling (under filling phenomenon takes place), putting the heart on the descending limb of the Starling curve and resulting in a decrease in cardiac output CO=SV·PR (see FIG. 1 and FIG. 2, where SV is a stroke volume), though the pacing rate PR goes higher. In the second form, an adequate cardiac output is maintained but the heart rate, and therefore the cardiac oxygen consumption, is greater than necessary to supply overall metabolic demand of myocardium. This can promote cardiac ischemia and, potentially, arrhythmias.

The under pacing phenomenon occurs when the sensed demand is low (e.g., during a deep sleep) and the paced heart rate is either insufficient to meet metabolic demand or the cardiac output is maintained primarily by increasing a preload (i.e., increasing end-diastolic volume and stroke volume) (U.S. Pat. No. 6,975,903). This situation was common in the early days of fixed-rate pacing. The accompanying increases in wall-stress can promote hypertrophy, fibrosis and heart failure.

The heart rate is critical because it is possible for metabolic demand to exceed the capabilities of the damaged heart. The artificial pacing system may drive the heart into failure while trying to meet the metabolic demand. Traditionally, the upper and lower pacing rate limits to avoid over and under pacing of the heart are determined by the implanting physician and are programmed into the pacemaker at the time of implanting the device. The actual values may be determined from exercise studies, from algorithms which take into account patient's characteristics, or from clinical experience and are set for every patient individually (Webster, above).

Incorrect rate limits or rate response can have serious impact on a patient's quality of life. For example, postural hypotension, a sudden drop in blood pressure caused by shifts in blood volume to the lower extremities due to a decrease in hydraulic resistance, $R_{body}$ (FIG. 1), when rising from a seated or supine posture, can lead to syncope and falling of the patient, or worse. Neurogenic syncope is a similar problem but even more insidious because the sudden drop in blood pressure may occur minutes after the precipitating event.

If the normal compensatory vasoconstriction is missing or remains insufficient, the condition may be ameliorated by increasing the heart rate. Obviously, the timing and the extent of the heart rate increase are important.

Figure 1:
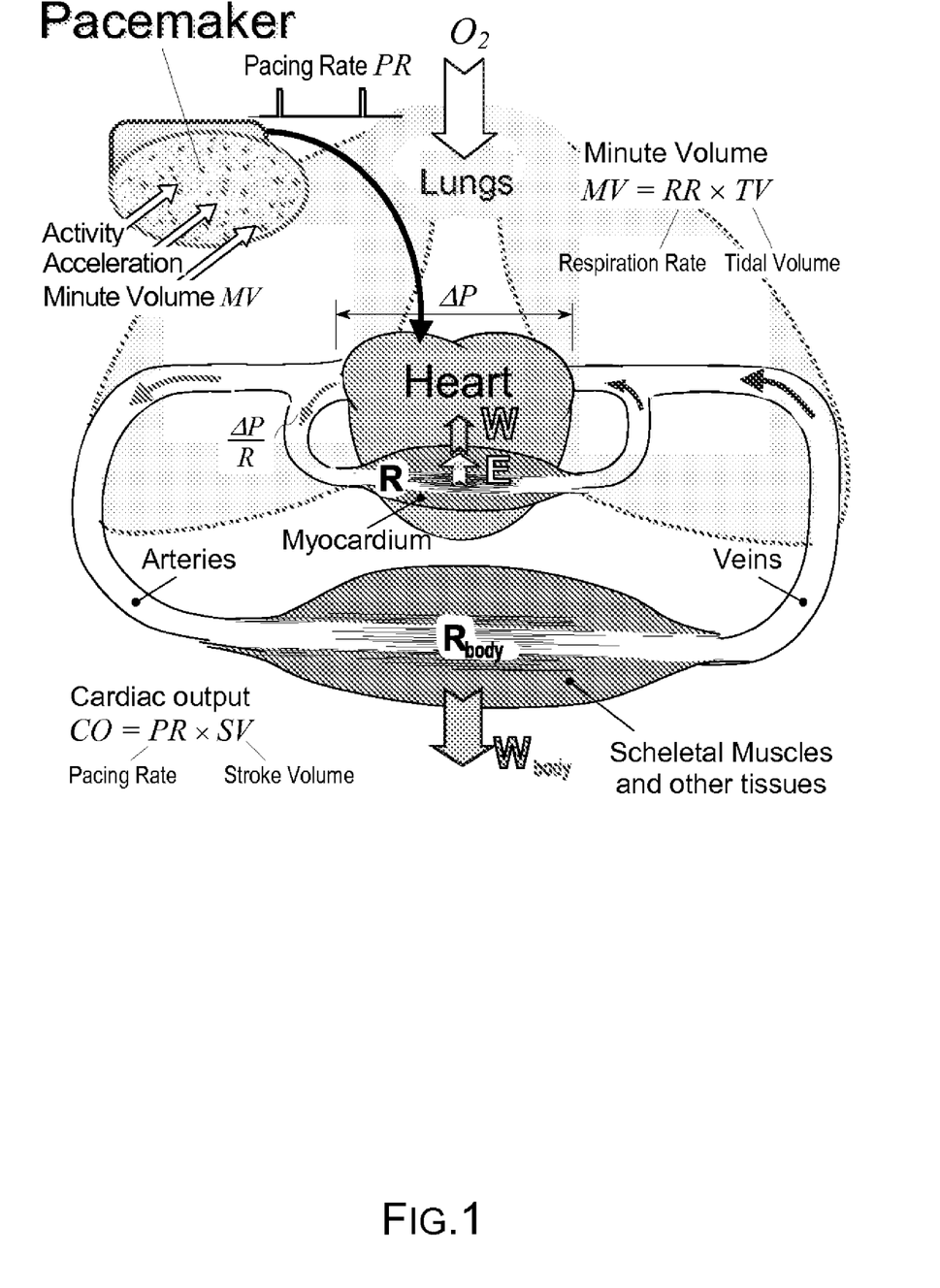
FIG. 1 is an implanted cardiac pacemaker with adaptive pacing rate control, and a simplified presentation of the cardiovascular system according to one embodiment.

Patient's upper rate limit is determined by the following factors. The ability of heart to work at higher rates is correlated with a better coronary reserve (CR), characterized with a capability to dilate coronary arteries and, therefore, to reduce the hydraulic resistance R of the myocardium (FIG. 1). Myocardium damaged during an ischemic event or by other disease (e.g., diabetes) has limited cardiac reserve and capability to cope with the rising cardiac demand W.

Figure 2:
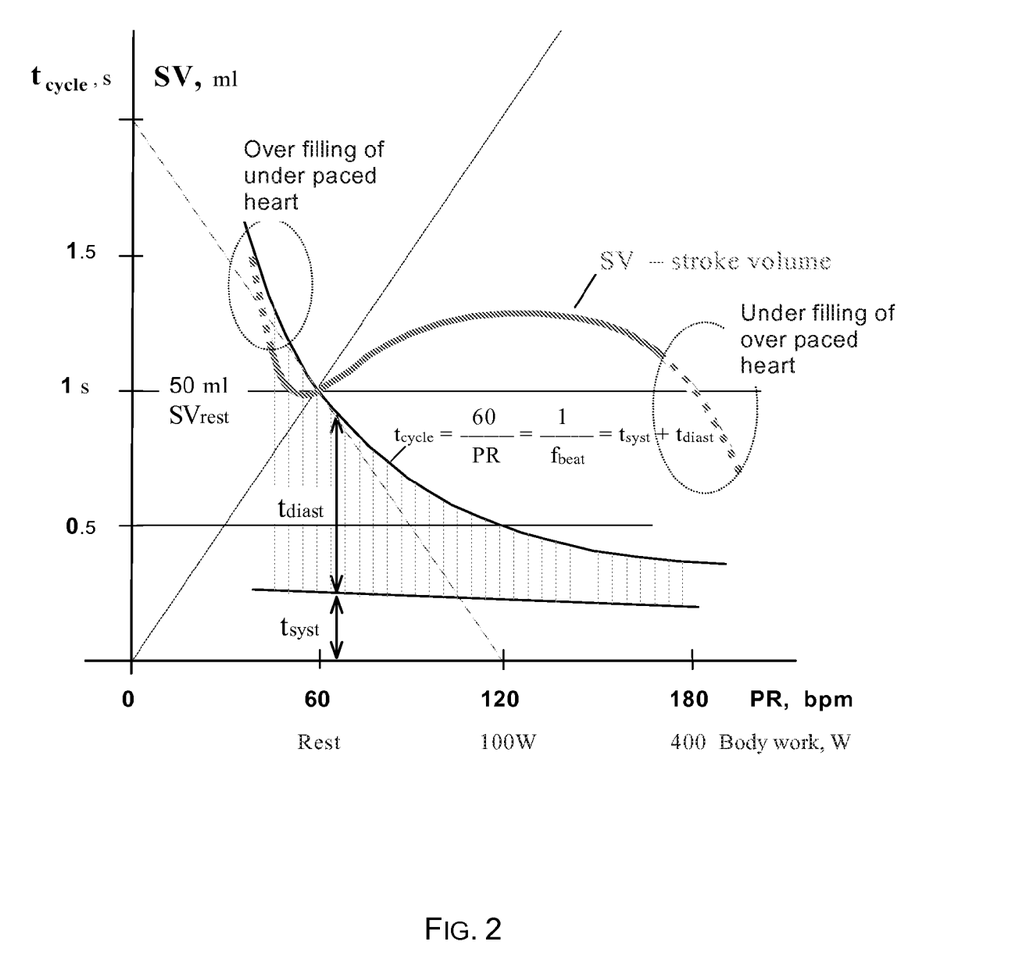
FIG. 2 shows the dependence of the stroke volume SV and diastolic time $t_{diast}$ on pacing rate PR according to one embodiment.

The ability to operate at low heart rates is determined by the ability of the heart to supply adequate cardiac output at rest, $CO_{rest} = SV_{rest} \cdot PR_{rest}$ (FIG. 1 and FIG. 2). Here the limitations occur during ventricular filling. A compliant heart with good diastolic function is able to increase end-diastolic volume with minimal increase in filling pressure and can double stroke volume, and therefore cardiac output, without a rate increase. This over filling phenomenon is accompanied by an increase in myocardial "stretch" and wall stress (see U.S. Pat. No. 6,975,903).

It is critical to maintain a balance between an energy demand W and a supply E in the heart (FIG. 1). Since insufficient myocardial perfusion will lead to hypoxia, ischemia, and infarct, under most circumstances the primary concern must be to maintain adequate cardiac perfusion and to guarantee that W is less than or equal to E.

A myocardial energy imbalance is determined as follows. Useful energy consumption, i.e., the external work W of the myocardium during a cardiac cycle can be characterized by the stroke work, the area $S_{dem}$ of the pressure-volume loop (PV-loop), which characterizes the relationship between ventricular volume V and ventricular pressure P, as shown in FIG. 3a. On the other hand, the energy supply E is proportional to the pressure difference between the aortic (or arterial) and ventricular pressure over the duration of diastole $t_{diast}$ (FIG. 2 and FIG. 3b). Therefore, the energy supply E is proportional to the area $S_{sup}$ in FIG. 2b.

More precisely, $S_{dem}$ is the external work done by the ventricle during a cardiac cycle $t_{cycle} = t_{diast} + t_{syst}$ (see FIG. 2) for pumping blood into the aorta (A. B. Ericsson, Cardioplegia and Cardiac Function Evaluated by Left Ventricular P-V Relations, PhD.thesis, Karolinska Institutet, Stockholm, Sweden, Stockholm, 2000. ISBN 91-628-4138-6; E. Söderqvist, Left ventricular volumetry technique applied to a pressure guide wire, Licentiate thesis, Royal Institute of Technology, Stockholm, Sweden, 2002. ISBN 91-7283-318-1). However, an additional work is required for storing potential energy into myocardium (cocking of myocardium's fibers). This is called an internal static work and is proportional to the roughly triangular area $S_{pot}$ in FIG. 4. Thus, the energy supply E to the myocardium must be slightly greater than or equal to the energy consumed by the myocardium for both the external dynamic work, i.e., for pumping blood into a vascular system, and the internal static work of the myocardium.

Therefore, there is a need for a device and a method that takes the internal static work into account when determining the myocardial energy balance.

Figure 4:
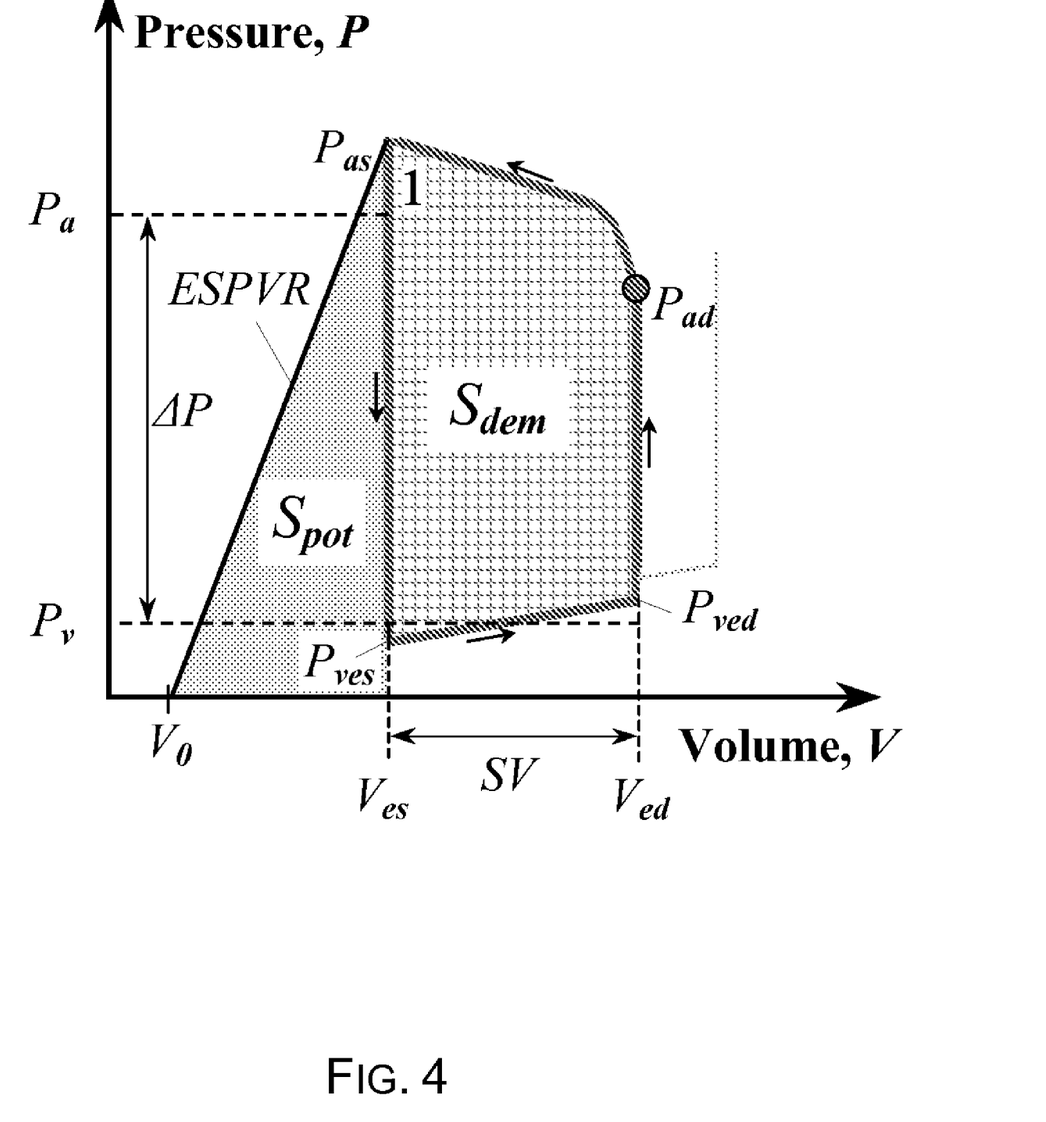
FIG. 4 shows a P-V diagram with energy consumption areas $S_{dem}$ (representing the energy consumed by the myocardium) and $S_{pot}$ (representing the internal static work of myocardium), where ESPVR is the end-systolic P-V relationship line and $V_0$ is a dead or useless volume of ventricle (unloaded heart), according to one embodiment.

FIG. 4 shows that blood pressure must be measured to determine both $S_{pot}$, proportional to the internal static work, and $S_{dem}$, proportional to the external work. However, constant measuring of blood pressure can be complex task.

Therefore, there is a need for a device and a method that determines the myocardial energy balance without the need for blood pressure measurements.

SUMMARY OF THE INVENTIONS

One aspect of the invention is a device for monitoring cardiac pacing rate, wherein the device comprises a measuring unit for receiving an electrical signal representing the patient's cardiac demand, and a computing unit for determining the myocardial energy balance by calculating energy consumed by the myocardium for both an external dynamic work for pumping blood into a vascular system, and internal static work of the myocardium. Volume and time based measurements are typically used. In one embodiment, volumes are estimated and volume ratios are calculated from volume estimates. In another embodiment, volumes are estimated from bioimpedance measurements.

Another aspect of the invention is a rate adaptive pacemaker, where the maximum pacing rate is determined from the myocardial energy balance where said energy supplied to the myocardium equals to the energy consumed by the myocardium for both the external dynamic work (for pumping blood into a vascular system), and internal static work of the myocardium.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposed, and not to limit the scope of the inventive subject matter.

DETAILED DESCRIPTION OF THE INVENTIONS

FIG. 1 depicts an implanted cardiac pacemaker with adaptive pacing rate control, and a simplified presentation of the cardiovascular system. The pacing rate must be adaptive to the patient's workload to ensure the required cardiac output CO, which is a product of stroke volume SV and heart rate HR. Several kind of body sensors monitor the level of physical work $W_{body}$, e.g., activity and acceleration sensors, and a sensor of minute volume MV of respiration. The most adequate means for estimating the workload is measurement of variations of the electrical bioimpedance of lungs. In simple cases the pacing rate (PR) follows almost linearly the minute volume (MV) of respiration, which can be obtained directly from the measured lung impedance. However, in more complicated cases the pacing rate PR has a badly defined nonlinear dependence from the respiration rate (RR) and the tidal volume (TV). The unhealthy heart can not operate at both, significantly high and low rates because of reducing of the myocardium's energy supply E (in comparison with energy consumption for work W), which is proportional to the blood inflow equal to $\Delta P/R$, where $\Delta P$ is the blood pressure difference, and R is the hydraulic resistance of the vascular system of the heart itself. The limits between which the heart is able to operate without any danger to the myocardium can vary depending on the actual status of an unstably operating diseased organism.

There are certain medical routines established for determining the maximum and minimum cardiac pacing rate values, allowable for the patient with a diagnosed disease. These settings are to be determined as the constants before implantation of the pacemaker, which are periodically re-programmable also after implantation.

The real maximum and minimum values for the heart rate can vary depending on the actual status of the heart and patient's health in general, and the pacing rate limits should be changeable accordingly to ensure well-being of patients.

The ability of heart to work at higher rates is correlated with a better coronary reserve (CR), characterized with a capability to dilate coronary arteries and, therefore, reduce the hydraulic resistance R of myocardium (FIG. 1). Myocardium damaged during an ischemic event or by other disease (e.g., diabetes) has a limited cardiac reserve.

The ability to operate at low heart rates is determined by the ability of the heart to supply adequate cardiac output at rest, $CO_{rest}=SV_{rest} \cdot PR_{rest}$ (FIG. 1 and FIG. 2). The limitations occur here during ventricular filling. Compliant hearts with good diastolic function are able to increase end-diastolic volume with minimal increase in filling pressure and can double stroke volume, and therefore cardiac output, without a rate increase. This over filling phenomenon is accompanied by an increase in myocardial "stretch" and wall stress (see U.S. Pat. No. 6,975,903).

The pacing rate control is accomplished so that it approximately follows the energy needs of patient's body $W_{body}$.

FIG. 3a shows a ventricular pressure-volume loop (marked as "a") and FIG. 2b shows the variation of arterial pressure (marked as "b"). Useful energy consumption or the external work W of the myocardium during a cardiac cycle can be characterized by the stroke work, the area $S_{dem}$ of the pressure-volume loop (PV-loop), which characterizes the relationship between ventricular volume V and ventricular pressure P, as shown in FIG. 3a. On the other hand, the energy supply E is proportional to the pressure difference between the aortic or arterial and ventricular pressure over the duration of diastole (diastolic time) $t_{diast}$ (FIG. 3b).

Therefore, the energy supply E is proportional to the area $S_{sup}$ in FIG. 3b. It can be seen, that smaller $S_{sup}$ correspond to higher pacing rate PR because of smaller duration of diastole $t_{diast}$ (see FIG. 2). Therefore, in certain heart rate the energy balance can no longer be maintained and further increase in pacing rate PR will drive the heart into a failure.

Figure 3:
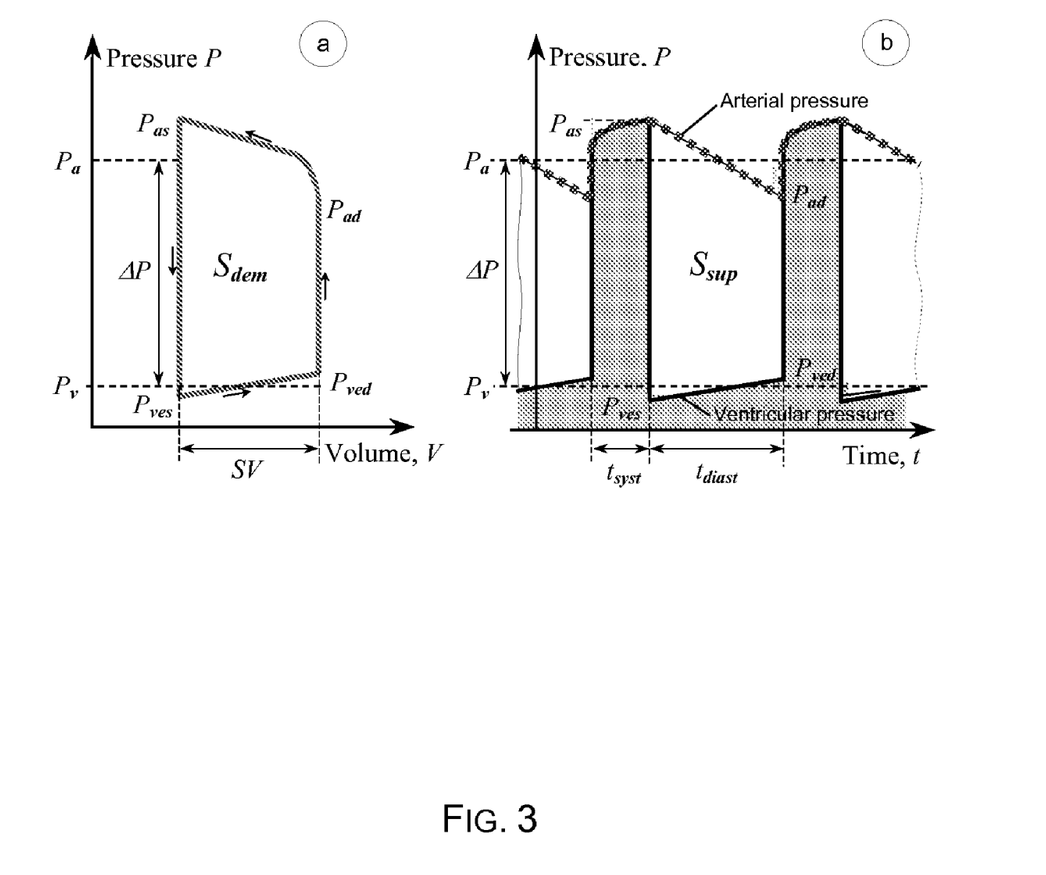
FIG. 3a shows the ventricular pressure-volume loop and FIG. 3b shows the variation of arterial pressure according to one embodiment.

More specifically, $S_{dem}$ is the external work done by the ventricle during a cardiac cycle pumping blood into the aorta. The roughly triangular area $S_{pot}$ between the average diastolic filling pressure line $P_v$ and the line defining the end-systolic pressure-volume relationship (ESPVR) in FIG. 3 is proportional to the potential energy requirement of myocardium $W_{pot}$—internal static work (S. Denslow, "Relationship between PVA and myocardial oxygen consumption can be derived from thermodynamics," Am J Physiol Heart Circ Physiol, Vol. 270, Issue 2, pp. H730-H740, 1996). The total energy consumption of myocardium can be expressed as the area $S_{cons}=S_{dem}+S_{pot}$, where $S_{pot}=(V_{es}-V_0)\cdot(P_{as}-P_{ves})/2$ is calculated from the triangle in FIG. 4 and where $V_0$ is the dead or useless volume of ventricle (unloaded heart).

The total energy consumption $S_{cons}$ of myocardium can be expressed as $S_{dem}\cdot k_{pot}$, where $k_{pot}$ determines the relative role of $S_{pot}$. The myocardial energy balance can be expressed as $S_{sup}=S_{dem}\cdot k_{pot}$, where $k_{pot}$ depends on relative stroke volume $SV/V_{es}$ (see FIG. 5).

Figure 5:
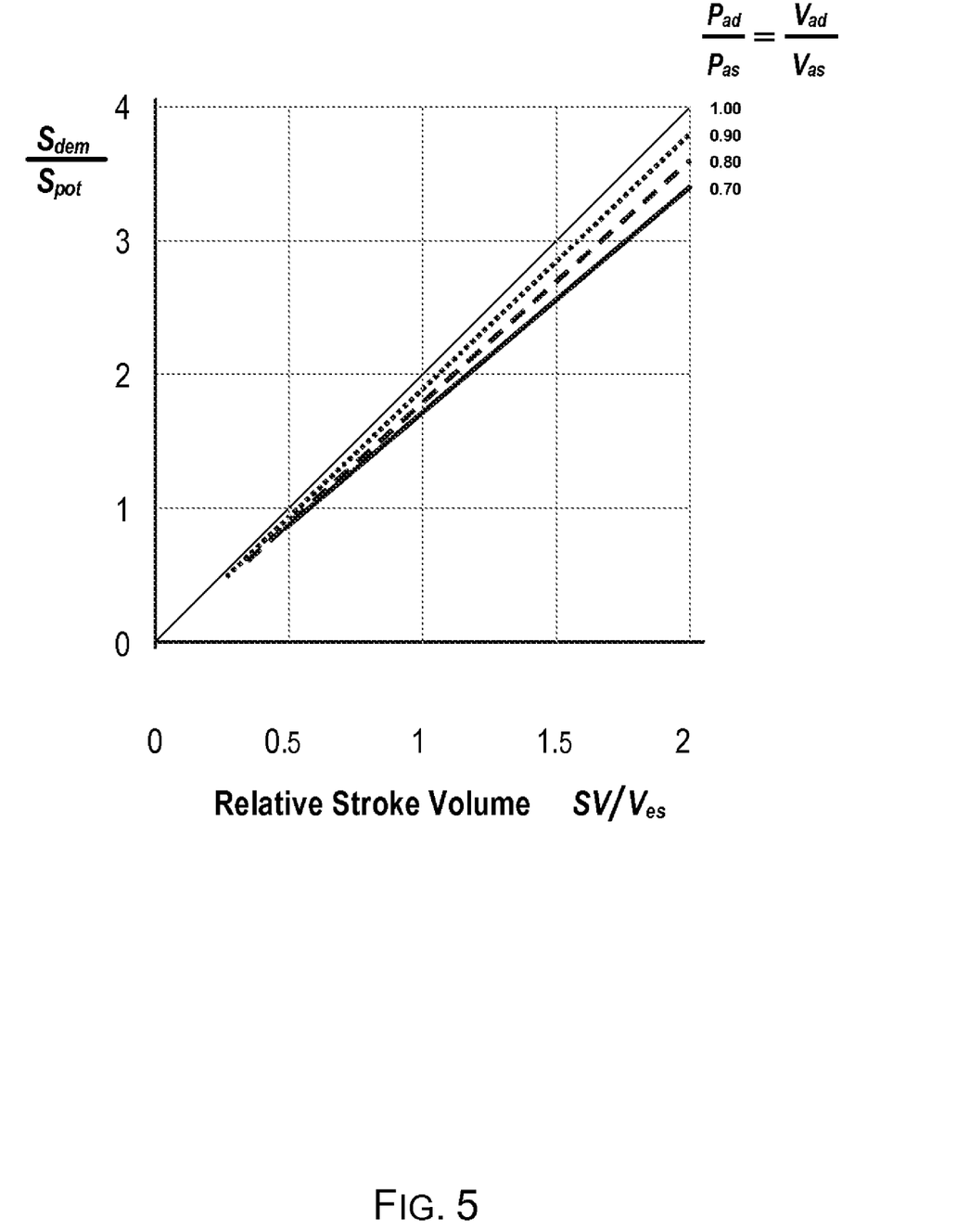
FIG. 5 shows a relationship of the relative energy demand $S_{dem}/S_{pot}$ versus the relative stroke volume $SV/V_{es}$ for several values of arterial pressures $P_{as}/P_{ad}$, derived from the simplified geometry in FIG. 4 according to one embodiment.

From the relationships illustrated in FIG. 5, and the ratio $P_{ad}/P_{as}$ of diastolic and systolic arterial pressures $k_{pot}=(S_{dem}+S_{pot})/S_{dem}=1+S_{pot}/S_{dem}$, at certain value of $P_{ad}/P_{as}$, it appears that the balance conditions depend only weakly on the systolic and diastolic arterial pressure values, $P_{as}$ and $P_{ad}$. We can, therefore, substitute for them the average arterial pressure Pa=(Pas+Pad)/2, see FIG. 3 and FIG. 4.

The pressure and the stroke volume is measured as follows. The area of the P-V diagram in FIG. 3a can be expressed approximately as $S_{dem}=\Delta P\cdot SV$, and the area $S_{sup}$ in b can be approximated as $\Delta P\cdot t_{diast}$, where $\Delta P$ is the mean difference between aortic and ventricular pressure. Finally, the area $S_{pot}$ can also be expressed in terms of $\Delta P$.

Since $S_{dem}+S_{pot}=S_{sup}$ at energy balance, $\Delta P$ drops out and it becomes unnecessary to make the pressure measurement for estimation the balance.

Thus to follow changes in energy balance it is necessary to measure only the stroke volume SV, end-systolic volume $V_{es}$, and the duration of diastole $t_{diast}$, see FIG. 3 and FIG. 4. The time interval $t_{diast}$ can be estimated from the ECG signal as the time from the T-wave to the R-wave, or may be derived from volume or pressure waveforms. Estimation of the stroke volume SV and $V_{es}$ requires more complicated measurements.

The energy demand $W_{body}$ of the patient's body is currently estimated in implantable devices by the minute volume (MV) (FIG. 1), determined through measurement of the electrical bioimpedance of the torso. Since impedance circuitry is currently available in these devices, it seems reasonable to try to assess stroke volume by the same technique.

It is known that impedance is a source of physiological information. Intracardiac impedance varies significantly with every stroke of the heart, and thus provides a cardiac signal component that can be considered to be an impedance cardiogram (ICG). The respiratory component of the impedance signal corresponds to changes in lung impedance during breathing and is typically used for pacing rate control because it reflects the minute volume MV (see FIG. 1). The cardiac component of the ICG can be used to estimate the stroke volume and to use this information to maintain energy balance by controlling the pacing rate.

As shown in U.S. Pat. Nos. 6,885,892 and 6,975,903, not only the absolute value of the SV but also the relative value of $SV/SV_{rest}$ or $V_{es}/V_{es,rest}$ can be useful in discerning an energy imbalance. This approach is technically simpler in that absolute accuracy of the volume measurement is not necessary. The results of laboratory experiments are promising (R. W. Salo, "Application of impedance volume measurement to implantable devices," International Journal of Bioelectromagnetism, Vol. 5, no. 1, pp. 57-60, January 2003. Available online: http://www.ijbem.org/volume5/number1/024.htm).

Numerical models have also demonstrated the feasibility of determining the ventricular volume, and particularly the SV from intracardiac impedance (R. W. Salo, "Accuracy of Conductance Catheter Measurements in a Realistic Numerical Heart Model: Validation of Reciprocal Equivalent Distance Extrapolation," International Journal of Bioelectromagnetism, Vol. 5, no. 1, pp. 61-62, January 2003. Available online: http://www.ijbem.org/volume5/number1/025.htm) using a multi-electrode left ventricular catheter. However, this catheter system is impractical for implantable devices due to the potential for thrombotic events.

The invention provides simple method for stabilizing of the stroke volume. In practice, it is difficult to predict the slope and intercept of the relationship between actual and computed volumes, but for this application it is only necessary to estimate relative changes in volume. Even just knowing the directions of changes (increasing or decreasing) is of interest when trying to stabilize the value of stroke volume (R. W. Salo, "Application of impedance volume measurement to implantable devices," International Journal of Bioelectromagnetism, Vol. 5, no. 1, pp. 57-60, January 2003. Online available: http://www.ijbem.org/volume5/number1/024.htm; R. W. Salo, "The theoretical basis of a computational model for the determination of volume by impedance," Automedica, vol. 11: pp. 299-310, 1989.), using a simple single-input and single-output (SISO) closed loop control system. The control system would be designed to maintain the actual stroke volume SV at the predetermined constant (reference) value $SV_{ref}$ which does not depend on the pacing rate.

Normally, there is a highly nonlinear relationship between the pacing rate PR and the corresponding stroke volume (see FIG. 2) during exercise. In closed loop systems, the pacing rate is adjusted automatically to a value, which satisfies the predetermined $SV=SV_{ref}$. The constant stroke volume means that the energy consumption of the myocardium will remain relatively constant for each heartbeat. At the same time, the energy supply diminishes with the shortening of the diastolic time $t_{diast}$ (FIG. 2) or corresponding increasing of the pacing rate $PR=60/(t_{syst}+t_{diast})$ in beats per minute (bpm).

The conditions for energy balance can be expressed directly through the pacing rate PR, knowing that in the case of balance between the energy consumption and supply a following equality takes place $k_{pot}\cdot(SV_{ref})\cdot\Delta P=(t_{diast})\cdot\Delta P$.

Substituting $t_{diast}=(60/PR)-t_{syst}$, it appears that the pacing rate must remain below $PR<60\ SV_{ref}/(1+k_{pot}\cdot SV_{ref}\cdot t_{syst})$ to avoid over pacing. This inequality is applicable in practice, because the systolic time $t_{syst}$ remains almost constant at different pacing rates (see FIG. 2).

Several control methods and different sensors are currently used in rate adaptive pacemakers to improve the quality of life of pacemaker patients. These devices are all used in an openloop manner and require sophisticated programming to meet patient needs under varying physiological conditions. It is possible to use hemodynamic information from bioimpedance measurements in a feed forward approach to control pacing rate while simultaneously monitoring myocardial energy balance to preclude potentially damaging heart rates. With this approach, the pacing rate is only available control tool for satisfying the patient's metabolic demands, on the one hand, and the myocardium's energy supply needs on the other. In addition, stabilizing stroke volume would maintain relatively constant preload and myocyte "stretch", minimizing hypertrophic signaling and subsequent cardiac remodeling.

The use of pacing in a population of patients with sick hearts demands increased concern over cardiac efficiency and maintenance of energy balance within the heart. These concerns may be addressed by a novel algorithm that requires only relative stroke volume information, derivable from bioimpedance measurements, applied to a feedback control system. New impedance measurement methods are expected to permit more reliable results to make such feedback systems feasible for rate control (R. W. Salo, S. O'Donoghue, E. V. Platia, "The use of intracardiac impedance-based indicators to optimize pacing rate," in Clinical Cardiac Pacing, K. A. Ellenbogen, G. N. Kay, and B. L. Wilkoff, Editors. Philadelphia, Pa.: W. B. Saunders Company, 1995, 234-249; M. Min, A. Kink, R. Land, T. Parve, "Method and device for measurement of electrical bioimpedance," US Patent Application Publication US 2006/0100539 A1, published May 11, 2006). Model based design appears to be a fruitful tool for the synthesis of complicated and nonlinear closed loop systems for pacing rate control.

Figure 6:
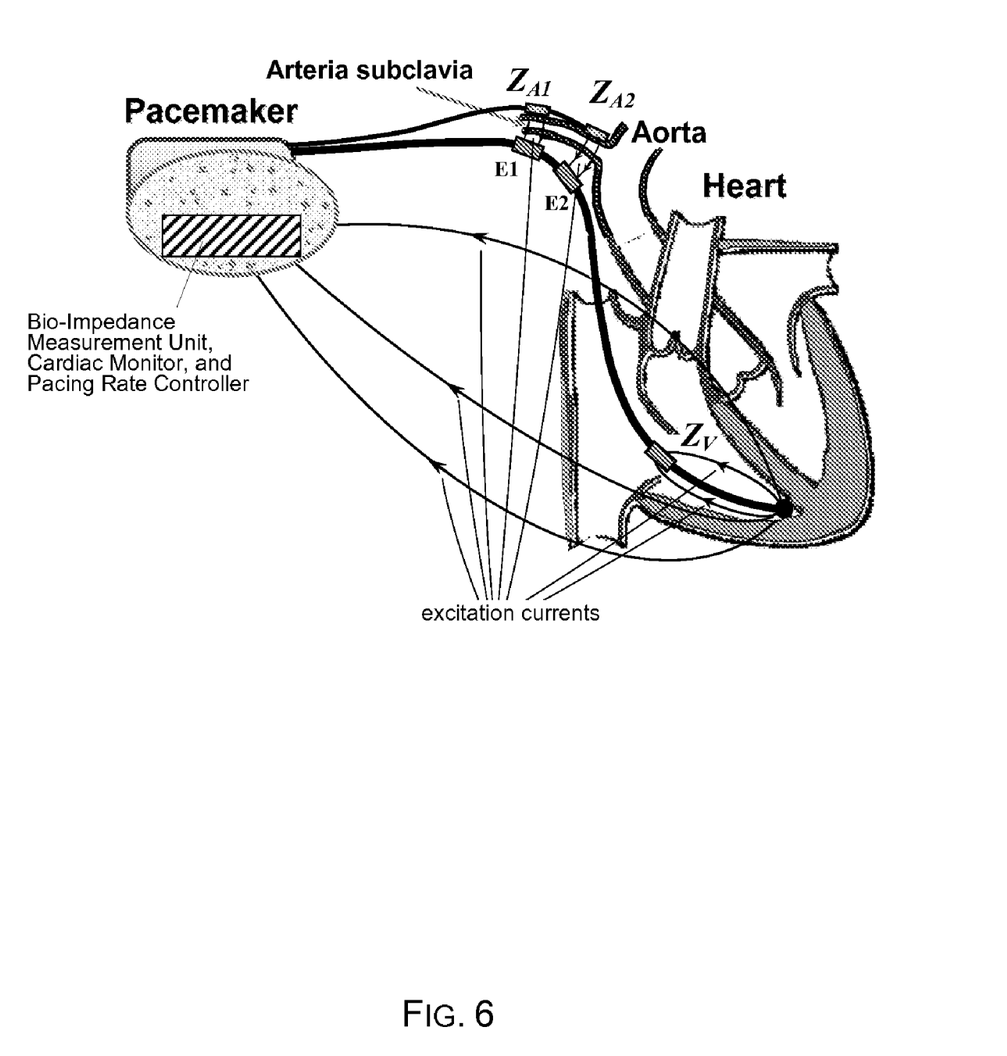
FIG. 6 shows an example of application of the proposed solution in a rate adaptive cardiac pacemaker, where $Z_V$ is a ventricular impedance, and $Z_{A1}$ and $Z_{A2}$ are arterial impedances. The electrodes E1 and E2 are introduced for measurement of arterial impedances.

FIG. 6 shows an example of application of the proposed solution in a rate adaptive cardiac pacemaker, where $Z_V$ is a ventricular impedance, and $Z_{A1}$ and $Z_{A2}$ are arterial impedances. The electrodes E1 and E2 are introduced for measurement of arterial impedances.

The ventricular impedance $Z_V$ characterizes ventricular volume, and $Z_A$ helps to estimate the ratio of diastolic and systolic arterial pressures through arterial volumes. The volumes are correlated with pressures:

diastolic arterial volume ($V_{ad}$)×indicator of arterial nonelasticity (stiffness)=diastolic arterial pressure ($P_{ad}$).

systolic arterial volume($V_{as}$)×indicator of arterial nonelasticity (stiffness)=systolic arterial pressure ($P_{as}$).

As a result, the ratio of volumes $V_{ad}$ and $V_{as}$ is proportional to the ratio of pressures:

$$V_{ad}/V_{as} \approx P_{ad}/P_{as},$$

because the indication of arterial nonelasticity (stiffness) has a constant value during a cardiac cycle and drops out, therefore.

This ratio is used for exact volume based calculations of cardiac energy and work parameters (see FIG. 5).

Using of several arterial impedances (multipoint measurement) enables to estimate other important diagnostic values, as velocity of pulse wave propagation, elasticity of arteries, arterial blood flow parameters, hydraulic resistance of periphery arteries, etc.

Although this invention is described with respect to a set of aspects and embodiments, modifications thereto will be apparent to those skilled in the art. The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed includes at least the following:

1. A device for monitoring a cardiac pacing rate, the device comprising:
    a measuring unit adapted for interaction with a subject for obtaining an electrical signal representing cardiac demand of said subject; and
    a computing unit supplied with said signal for determining a relation between an energy supplied to a myocardium and an energy consumed by the myocardium, and calculating a maximum pacing rate from said relation so that said maximum pacing rate corresponds to a myocardial energy balance where said energy supplied to the myocardium equals to said energy consumed by the myocardium for both an external dynamic work for pumping blood into a vascular system, and an internal static work of the myocardium, wherein a ratio of a diastolic pressure and a systolic pressure is calculated and said ratio is used to calculate said energy consumed by the myocardium.

2. The device as in claim 1, wherein said energy consumed by the myocardium is calculated from a stroke volume SV and an end-systolic volume $V_{es}$.

3. The device as in claim 1, wherein said myocardial energy balance is calculated from a stroke volume SV, an end-systolic volume $V_{es}$, and a duration of a diastole $t_{diast}$.

4. The device as in claim 1, wherein said internal static work of the myocardium is calculated from its unloaded volume $V_0$ and end-systolic volume $V_{es}$.

5. The device as in claim 1, wherein said electrical signal is obtained through bioimpedance measurement.

6. The device as in claim 2, wherein said volumes are estimated based on bioimpedance measurement.

7. The device as in claim 1, wherein said ratio of said diastolic pressure and said systolic pressure is calculated from a ratio of a systolic volume and a diastolic volume in a blood vessel.

8. The device as in claim 7, wherein said blood vessel is an aorta or an artery.

9. The device as in claim 8, wherein said blood vessel is subclavian artery.

10. The device as in claim 7, comprising at least a pair of electrodes on said blood vessel for measuring of a systolic bioimpedance and a diastolic bioimpedance and calculating said ratio based on said systolic bioimpedance and said diastolic bioimpedance.

11. The device as in claim 2, comprising ultrasound sensors for volume measurements.

12. The device as in claim 3, wherein said duration of a diastole $t_{diast}$ is measured from an electrocardiogram.

13. The device as in claim 3, wherein said duration of a diastole $t_{diast}$ is measured from an impedance cardiogram.

14. The device as in claim 10, said pair of electrodes arranged to measure and to estimate a velocity of a pulse wave propagation.

15. The device as in claim 10, said pair of electrodes arranged to measure and to estimate an elasticity of arteries.

16. The device as in claim 10, said pair of electrodes arranged to characterize a blood flow into peripheral arteries and to estimate their hydraulic resistance to the blood flow.

17. The device as in claim 5, comprising at least one intracardiac implanted electrode for bioimpedance measurement.

18. The device as in claim 5, comprising noninvasive impedance cardiography electrodes for volume measurements.

19. A device for monitoring a cardiac pacing rate, the device comprising:

a measuring unit adapted for interaction with a subject for obtaining an electrical signal representing cardiac demand of said subject; and a computing unit supplied with said signal for determining a relation between an energy supplied to a myocardium and an energy consumed by the myocardium, and calculating a maximum pacing rate from said relation so that said maximum pacing rate corresponds to a myocardial energy balance where said energy supplied to the myocardium equals to said energy consumed by the myocardium for both an external dynamic work for pumping blood into a vascular system, and an internal static work of the myocardium, wherein said maximum pacing rate is 60 $SV_{ref}/(1+k_{pot} \cdot SV_{ref} \cdot t_{syst})$, where $SV_{ref}$ where $SV_{ref}$ is a predetermined stroke volume, $k_{pot}$ is a constant, representing the relative role of said internal static work of the myocardium compared to said external dynamic work, and $t_{syst}$ is a systolic time.

20. A rate adaptive pacemaker, comprising:

a measuring unit adapted for interaction with a subject for obtaining an electrical signal representing a cardiac demand of said subject;

a pacing rate controller, connected to said measuring unit for controlling a pacing rate in response to said cardiac demand;

a pacing rate limiter, connected to said pacing rate controller, said pacing rate limiter having an upper limit setting unit for setting an upper limit value for said pacing rate, and an upper limit determining unit for determining a relation between energy supplied to the myocardium and energy consumed by the myocardium, and for calculating said upper limit value from said relation for supply to said upper limit setting unit, said pacing rate limiter upwardly limiting said pacing rate to always maintain a myocardial energy balance where said energy supplied to the myocardium equals to said energy consumed by the myocardium for both an external dynamic work for pumping blood into a vascular system, and an internal static work of the myocardium, wherein said upper pacing rate is 60 $SV_{ref}/(1+k_{pot} \cdot SV_{ref} \cdot t_{syst})$, where $SV_{ref}$ is a predetermined stroke volume, $k_{pot}$ is a constant, representing the relative role of said internal static work of the myocardium compared to said external dynamic work, and $t_{syst}$ is a systolic time.

21. The device as in claim 20, said measuring unit adapted to receive and process bioimpedance signals.

22. The device as in claim 21, comprising a calculating unit, supplied with a signal from said measuring unit to discover and monitor an oedema of myocardium and lungs with bioimpedance measurements at different frequencies.

23. The device as in claim 20, comprising a communication unit for transmitting diagnostic parameters.

* * * * *